United States Patent [19]

Sunshine et al.

[11] Patent Number: 4,883,818

[45] Date of Patent: Nov. 28, 1989

[54] ONSET-HASTENED/ENHANCED ANALGESIA

[75] Inventors: Abraham Sunshine, New York; Eugene M. Laska, Larchmont, both of N.Y.

[73] Assignee: Analgesic Associates, Larchmont, N.Y.

[21] Appl. No.: 121,848

[22] Filed: Nov. 17, 1987

[51] Int. Cl.⁴ .............................................. A61K 31/19
[52] U.S. Cl. .................................... 514/570; 514/571
[58] Field of Search ................................ 514/570, 571

[56] References Cited

U.S. PATENT DOCUMENTS

| | | | |
|---|---|---|---|
| 3,600,437 | 8/1971 | Marshall | 260/50 |
| 3,637,767 | 1/1972 | Alvarez | 260/348 R |
| 4,440,787 | 4/1984 | de Vincentiis | 424/319 |
| 4,464,376 | 8/1984 | Sunshine et al. | 424/253 |
| 4,501,727 | 2/1985 | Armitage et al. | 424/253 |
| 4,542,237 | 9/1985 | Schloemer | 424/253 |
| 4,552,899 | 11/1985 | Sunshine et al. | 424/253 |
| 4,558,051 | 12/1985 | Sunshine et al. | 424/253 |
| 4,619,934 | 10/1986 | Sunshine et al. | 424/253 |
| 4,722,938 | 2/1988 | Sunshine et al. | 424/253 |

FOREIGN PATENT DOCUMENTS 0205215 12/1986 European Pat. Off. .

OTHER PUBLICATIONS

"Stereoselective Inversion of (R)-Fenoprofen to (S)-Fenoprofen in Humans", *Journal of Pharmaceutical Sciences*, A. Rubin et al., vol. 74, No. 1, Jan. 1985, pp. 82–84.

"Importance of Drug Enantiomers in Clinical Pharmacology", *Drugs*, Kenneth Williams et al., vol. 30 (1985), pp. 333–354.

"Enantioselective Disposition of 2-Arylpropionic Acid Nonsteroidal Anti-Inflammatory Drugs. III. Fenoprofen Disposition", *The Journal of Pharmacology and Experimental Therapeutics*, P. J. Hayball et al., vol. 240, No. 2 (1987), pp. 631–636.

"Isomeric Inversion of Ibuprofen (R)-Enantiomer in Humans", *Journal of Pharmaceutical Sciences*, D. G. Kaiser et al., vol. 65, No. 2, Feb. 1976, pp. 269–273.

"Enantiospecific High-Performance Liquid Chromatographic Analysis of 2-Phenylpropionic Acid, Ketoprofen and Fenoprofen", *Journal of Chromatography*, B. C. Sallustio et al., vol. 374 (1986), pp. 329–337.

"The Metabolic Chiral Inversion of 2-Arylpropionic Acids—A Novel Route with Pharmacological Consequences", *J. Pharm. Pharmacol.*, Andrew J. Hutt et al., vol. 35 (1983), pp. 693–704.

"The Importance of Stereochemistry in the Clinical Pharmacokinetics of the 2-Arylpropionic Acid Non-Steroidal Anti-Inflammatory Drugs", *Clinical Pharmacokinetics*, Andrew J. Hutt et al., vol. 9 (1984), pp. 371–375.

"Naproxen", *Anti-Inflammatory and Anti-Rheumatic Drugs*, Anthony C. Allison, et al., vol. 11, Chapter 9, Ed.: K. D. Rainsford, CRC Press, Inc., Boca Raton, Florida, p. 172.

"Gas Chromatographic Separation of Optically Active Anti-Inflammatory 2-Arylapropionic Acids Using (+)- or (−)-Amphetamine as Derivatizing Reagent", *J. Chromatogr. Biomed. Appl.*, N. N. Singh, et al., vol. 378, No. 1 (1986), pp. 125–135.

"The Resolution of Enantiomeric Drugs Using HPLC Chiral Stationary Phases", *Pharm. Technol.*, T. D. Doyle et al., vol. 9, No. 2 (1985), pp. 28–32.

"Application of High-Performance Liquid Chromatographic Chiral Stationary Phases to Pharmaceutical Analysis: Structural and Conformational Effects in the Direct Enantiomeric Resolution of Alpha Methylarylacetic Acid Antiinflammatory Agents", *J. Chromatogr.*, I. W. Wainer, et al., vol. 284, No. 1 (1984), pp. 117–124.

*Physician's Desk Reference*, 41st Edition (1987), Publisher: Edward A. Barnhart, Medical Economics Company, Inc., Oradell, N.J. 07649, pp. 890–891.

*Primary Examiner*—Stanley J. Friedman
*Attorney, Agent, or Firm*—Burns, Doane, Swecker & Mathis

[57] ABSTRACT

Onset-hastened and enhanced analgesic response is elicited in a mammalian organism in need of such treatment, i.e., a mammal suffering pain, by administering thereto a unit dosage onset-hastening/enhancing analgesically effective amount of the S(+) fenoprofen enantiomer, said enantiomer being substantially free of its R(−) fenoprofen antipode.

41 Claims, No Drawings

ONSET-HASTENED/ENHANCED ANALGESIA

CROSS-REFERENCE TO COMPANION APPLICATIONS

Our copending applications, Ser. No. 071,914, filed July 10, 1987, and Ser. No. 121,849 filed concurrently herewith, both assigned to the assignee hereof

BACKGROUND OF THE INVENTION

1. Field of the Invention:

The present invention relates to the use of S(+) fenoprofen to elicit an onset-hastened and enhanced analgesic response in mammalian organisms in need of such treatment, and to certain pharmaceutical compositions comprising unit dosage effective amounts of S(+) fenoprofen.

2. Description of the Art:

Fenoprofen, also known as α-dl-2-(3-phenoxyphenyl)-propionic acid or (±)-m-phenoxyhydratropic acid, has the structural formula

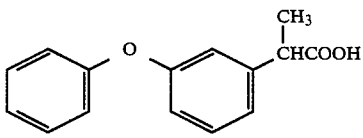

The compound is well-known as a nonsteroidal anti-inflammatory drug having analgesic and antipyretic activity. In the United States, fenoprofen is marketed as the calcium salt dihydrate under the tradename Nalfon ®. Other tradenames or codenames for fenoprofen calcium salt dihydrate include Lilly 69323, Fenopron, Feprona, Nalgesic and Progesic. As Nalfon ®, the drug is available by prescription in amounts equivalent to 200 mg or 300 mg (capsules) or 600 mg (tablets) of fenoprofen. For the treatment of mild to moderate pain, 200 mg every four to six hours, as needed, is generally recommended. For rheumatoid arthritis and osteoarthritis, 300 to 600 mg three or four times a day is the recommended dosage, not to exceed 3200 mg daily. See also *Physician's Desk Reference,* 41st edition, 1987, publisher Edward R. Barnhart, Medical Economics Company, Inc., Oradell, N.J. 07649, pp. 890–891.

As is apparent from its chemical nomenclature, fenoprofen is a racemic mixture It is only the racemic mixture which has in fact ever been marketed. There have, however, been a few studies of the individual S(+) and R(−) isomers reported in the literature. These generally reflect that the R(−) isomer is rapidly converted to the S(+) enantiomer, which is the active form of fenoprofen.

Hutt et al, *J. Pharm. Pharmacol.,* 35, 693–704 (1983), reviewed the earlier work on the metabolic chiral inversion of 2-arylpropionic acids, including ibuprofen, which they indicate was the first substituted 2-arylpropionic acid conclusively shown to undergo the inversion as well as the most studied member of the group. The authors noted that early workers found no significant difference in in vivo activity among the R(−) and S(+) isomers and the racemic mixture of ibuprofen in three different animal models, but very large differences in vitro between the R(−) and S(+) isomers, ascribing this discrepancy to the virtually quantitative conversion of the R(−) to the active S(+) isomer in vivo. Hutt et al indicated similar properties for fenoprofen. While no reports of the chiral inversion of fenoprofen had appeared at that time, the enantiomers of fenoprofen were reported to be of equal potency in animal test systems; moreover, it was noted that fenoprofen was known to undergo incorporation in triglycerides, an indirect indication of chiral inversion.

In the same paper, Hutt et al reported that, in contrast, for several other 2-arylpropionic acids, the inactive R(−) isomer was not converted in vivo to the active S(+) isomer as readily as ibuprofen and fenoprofen, although the conversion seemed to occur to some extent over time. Naproxen, they noted, has been the only compound marketed as the S(+) enantiomer to date. And in the case of indoprofen, the R(−) enantiomer was found to be about 20 times less pharmacologically active in rats and mice in vivo than the S(+) isomer. Hutt et al concluded:

It is likely that benefits will be obtained from the use of the S(+)-enantiomer of 2-arylpropionates as drugs as opposed to the racemates. This is only found at present in the case of naproxen. In cases of rapid inversion, the inactive R(−) isomer serves merely as a prodrug for the active S(+)-antipode. Where inversion is slow, the R(−) enantiomer is an unnecessary impurity in the active S(+) form. Use of the S(+)-enantiomer would permit reduction of the dose given, remove variability in rate and extent of inversion as a source of variability in therapeutic response and would reduce any toxicity arising from non-stereospecific mechanisms.

Thus, in cases of rapid inversion, such as ibuprofen and fenoprofen, where substantially equivalent in vivo responses have been reported for the individual enantiomers and the racemic drug, Hutt et al suggested that no benefits would be obtained from the use of the S(+) isomer because the inactive R(−) isomer merely acts as a prodrug for the active S(+) form. Contrariwise, in cases where chiral inversion is slow, e.g. naproxen and indoprofen, the use of the S(+) enantiomer is desirable for several reasons enumerated by Hutt et al. Indeed, naproxen has been reported to be marketed as the d-isomer for one of the reasons given by Hutt et al, i.e. to reduce side effects (Allison et al, "Naproxen," Chapter 9 in *Anti-inflammatory and Anti-Rheumatic Drugs,* eds. Rainsford and Path, CRC Press Inc., Boca Raton, Florida, 1985, p. 1 72).

Another general report on earlier work has been provided by Hutt et al in *Clinical Pharmacokinetics,* 9, 371–373 (1984). In this article on the importance of stereochemical considerations in the clinical pharmacokinetics of 2-arylpropionic acids, the authors tabulated relative potencies of the enantiomers of a number of 2-arylpropionic acids in vivo and in vitro The in vitro results showed the S or (+) isomer in each case to be the active species. In vivo, however, the results were not consistent across the entire class. Thus, the results for naproxen and indoprofen demonstrate the S on (+) isomer to be much more active in vivo, indicating a relatively slow inversion of the inactive R or (−) isomer to the active S or (+) isomer; the results for fenoprofen and ibuprofen, on the other hand, demonstrate the inactive R or (−) and the active S or (+) isomers to be approximately equally effective in vivo, indicating a rapid inversion of R or (−) isomer to S or (+) isomer. References for the fenoprofen test results cited by Hutt et al include Nicklander et al, *Federation Proceedings* 30, 563 (1971) and Rubin et al, *J. Pharm. Sci.* (in press, 1984). The Rubin et al reference, which was actually published in 1985, is discussed in detail below.

Rubin et al, *J. Pharm. Sci.* 74 (1), 82–84 (1985), studied the stereoselective inversion of R(−) fenoprofen to S(+) fenoprofen in healthy human volunteers. The authors administered the calcium salt of racemic fenoprofen orally and determined the amounts of R and S isomers in plasma and urine and the amounts of 4′-hydroxy metabolites in urine at various time points after administration. The R(−) isomer was found to be stereoselectively inverted to S(+), the major isomeric form found in plasma and urine. It was observed that 78–86% of administered fenoprofen racemate was recovered as S(+) fenoprofen plus the S-4′-hydroxy metabolite. In in vitro testing, the S enantiomer was found to be about 35 times as active at inhibiting cyclooxygenase as the R isomer and twice as active as the racemate. Rubin et al noted that earlier studies in the rat, mouse and guinea pig by Nicklander et al and others showed no difference in vivo in pharmacological and toxicological anti-inflammatory activities for the enantiomers, and indicated that those results may mean that the R(−) isomer is inverted quickly to the S(+) isomer in animals, as in man. Since the earlier studies did not analyze plasma or urine for individual isomers, Rubin et al qualitatively analyzed urine from rats, mice and guinea pigs dosed with racemic fenoprofen and found the excreted drug forms to be almost totally of the S configuration.

Williams et al, Drugs 30,333–354 (1985), reviewed the importance of drug enantiomers in clinical pharmacology generally. With respect to fenoprofen, the authors noted Rubin et al's work (discussed above) as being flawed because only racemic drug was administered and thus relative clearances and fractions inverted were uncertain. Nevertheless, Rubin et al did demonstrate the apparent avidity of the inversion process for fenoprofen, which Williams et al cited as "an example of a drug for which total racemic drug concentrations are very similar to the concentration of the active drug."

The enantioselective disposition of fenoprofen in normal rabbits was studied by Hayball et al, *J. Pharmacol. Exp. Ther.*, 240 (2), 631–636 (1987). These authors administered the R and S isomers of fenoprofen separately as well as the racemic mixture. Blood samples were collected before and at about 0.25, 1, 3, 5, 7, 10, 15, 20, 25, 30 minutes, then at 15 minute intervals until 120 minutes after dosing with S(+) fenoprofen. Similar time points were selected for R(−) and racemic fenoprofen blood samples. No S to R inversion was noted, but at two hours an average of 73% of R was inverted to S, although large interanimal variations (from 30.4 to 100%) were noted. The authors noted that their bound plus unbound fenoprofen concentration data had its limitations; if fenoprofen enantiomers bind to rabbit plasma stereoselectively, then their estimates of the clearance and distribution of the individual enantiomers would be biased. While there is no clear literature on whether fenoprofen exhibits stereoselective binding, it is quite likely that it does. It would have been desirable to measure unbound fenoprofen; unfortunately, the assay methodology was not of sufficient sensitivity to allow such measurements.

In summary, the current state of the art recognizes that, in mammals, the S(+) form is the active enantiomer of fenoprofen. The art further recognizes that there is a significant, relatively rapid conversion in vivo of R(−) to S(+), with no noted conversion of S(+) to R(−). Furthermore, in the only animal experiments on efficacy reported in the literature, it was noted that there were no significant differences in potency between the racemate and the enantiomers. This is attributed to the rapidity of the chiral inversion. This would suggest there would be no benefit to be derived from the use of S(+) fenoprofen alone for analgesia. The prior art, moreover, is conspicuously silent in respect to any onset-hastened/enhanced alleviation of mammalian pain utilizing whatever form of the fenoprofen drug species.

SUMMARY OF THE INVENTION

Surprisingly, the present inventors now find that S(+) fenoprofen can be advantageously administered to mammals suffering from pain, especially humans, to not only elicit a more potent analgesic response but also to evoke such response more rapidly than possible by administration of the same dose of fenoprofen in its racemic form.

This is particularly surprising in light of the art's failure to attribute any significative difference in activity in vivo for S(+) fenoprofen versus the racemic mixture, a failure which the present inventors brand as resulting from the lack of telling observations of the pain level or amount of relief at meaningful time points sufficiently soon after dosing in an appropriate analgesic model.

In one aspect, the present invention thus provides a method of hastening the onset of analgesia in a mammal, said method comprising administering to a mammal in need of such treatment an effective onset-hastening analgesic amount of S(+) fenoprofen substantially free of R(−) fenoprofen.

In another aspect, the present invention provides a method of eliciting an enhanced analgesic response in a mammal, particularly shortly after dosing, said method comprising administering to a mammal in need of such treatment an effective analgesia enhancing amount of S(+) fenoprofen substantially free of R(−) fenoprofen.

In yet another aspect, the present invention provides a pharmaceutical composition of matter for use in eliciting an onset hastened and enhanced analgesic response in mammals, especially humans, said composition comprising an effective analgesic unit dosage amount of S(+) fenoprofen substantially free of R(−) fenoprofen. Typically, S(+) fenoprofen is associated with a nontoxic pharmaceutically acceptable inert carrier or diluent therefor.

DETAILED DESCRIPTION OF THE PREFERRED EMBODIMENTS OF THE INVENTION

The term "fenoprofen" or "racemic fenoprofen" as used herein is intended to encompass not only α-dl-2-(3-phenoxyphenyl)propionic acid itself but also any pharmaceutically acceptable salt thereof, e.g. fenoprofen calcium dihydrate.

The term "S(+) fenoprofen" as used herein is intended to encompass not only the dextrorotatory or S(+) isomer of α-2-(3-phenoxyphenyl)propionic acid but also any pharmaceutically acceptable, analgesically effective salt thereof. The expression "substantially free of R(−) fenoprofen" as used in conjunction with the term "S(+) fenoprofen" means that the S(+) fenoprofen is sufficiently free of R(−) fenoprofen "which is the levorotatory form or R(−) isomer of α-2-(3-phenoxyphenyl)-propionic acid or salt thereof" to exert the desired onset-hastened and enhanced analgesic effect. Practically speaking, this means that the active ingredient should contain at least 90% by weight S(+) fenoprofen and 10% or less by weight R(−) fenoprofen. Preferably, the weight ratio of S(+) fenoprofen to R(−) fenoprofen is greater than 20:1, more preferably greater than 97:3. Most preferably the S(+) fenoprofen is 99 or more % by weight free of R(−) fenoprofen, i.e., the weight ratio of S to R is approximately equal to or greater than 99:1.

Where specific amounts of S(+) fenoprofen are set forth below, it should be understood that, unless otherwise specified, the amounts are given in mg of the acid, not of a salt. Moreover, unless otherwise specified, for simplicity's sake the amounts given represent total fenoprofen content, most of which is in the S(+) form. For example, "300 mg S(+) fenoprofen" means 300 mg total fenoprofen at least 90% of which is in the S(+) form, preferably at least 95%, more preferably at least 97% and most preferably 99% or more.

S(+) fenoprofen, in accord with the present invention, produces the following unexpected results:

(1) the analgesic effect of fenoprofen on the mammal is brought on more quickly than by use of the same dose of racemic fenoprofen; and (2) a greater analgesic response is elicited in the early hours than is elicited by the same dose of racemic fenoprofen.

These unexpected results can be achieved in the treatment of pain responsive to an NSAID (non-steroidal antiinflamatory drug) and specifically pain associated with inflammation. This includes postpartum and postoperative pain, dental pain, headache pain, dysmenorrhea, pain of musculoskeletal origin and pain and discomfort associated with respiratory infections such as colds and flu.

For patients suffering from such pain, who require treatment at a particular dose of racemic fenoprofen, the time from administration of medication to the onset of effective relief is clearly of paramount importance. The present inventors' discovery that S(+) fenoprofen, when used in place of racemic fenoprofen at the same dose, substantially shortens the onset time (i.e., substantially hastens the onset) of analgesia is therefore very significant. It is likewise quite unexpected. Moreover, in patients suffering from inflammatory or degenerative joint disease, e.g. rheumatoid arthritis, osteoarthritis, gout or acute musculo-skeletal disease, the substantial shortening of analgesic onset is extremely important; pain is an important component of these disease states and more rapid relief from pain is of substantial psychological benefit. The S(+) fenoprofen will, of course, over time provide relief from other aspects of inflammatory disease as well, including, e.g. morning stiffness.

In a group responsive to a given dose of the racemate, it is believed that onset time for analgesia can be reached, on the average, about one-third sooner when S(+) fenoprofen is used rather than when racemic fenoprofen is administered, depending on the dose level and the severity of the pain, but particularly at the low end (25–200 mg) of the analgesic dosage range and for patients with moderate pain.

Insofar as concerns enhanced analgesia, more pronounced analgesia is obtained when S(+) fenoprofen is used at the same dose level as racemic fenoprofen, especially during the first few hours.

The precise amount of S(+) fenoprofen for use in accord with the present invention will vary depending, for example, on the size and kind of the mammal and the condition for which the drug is administered. For use in humans, the analgesically effective amount of S(+) fenoprofen will typically be from about 25 to 600 mg, although greater amounts (e.g. 800 mg) may be employed if needed for pain relief and if tolerated by the patient. The daily dose in humans preferably will not exceed 3200 mg S(+) fenoprofen, although greater amounts could be employed if tolerated by the patient. Preferred unit dosage compositions for use in the treatment of mild to moderate pain having an inflammatory component contain 25, 50, 100, 150, 200, 300, 400 or 600 mg S(+) fenoprofen.

While the compositions for use in the invention are preferably for oral use, they may also be formulated for and administered by other routes which are known for administering non-narcotic analgesics/nonsteroidal anti-inflammatory drugs, e.g. as suppositories or parenteral solutions, or as topical formulations such as ointments, gels, creams, lotions, solutions, impregnated bandages or other topical delivery devices, and so forth. Also, it should be noted that the preferred human dosage levels indicated above are for use in adults; pediatric compositions would contain proportionately less of the active ingredient.

The compositions for use herein are very conveniently administered to mammals by any route of administration suitable for racemic fenoprofen, e.g. oral, rectal, topical or parenteral. Preferably S(+) fenoprofen is formulated with any suitable nontoxic pharmaceutically acceptable inert carrier material. Such carrier materials are well known to those skilled in the art of pharmaceutical formulations. For those not skilled in the art, reference is made to the text entitled *Remington's Pharmaceutical Sciences*, 17th edition, 1985, ed. Alfonso R. Gennaro, Mack Publishing Company, Easton, Pennsylvania 18042. In a typical preparation for oral administration, e.g. tablet, capsule or caplet, S(+) fenoprofen in an effective analgesic amount and substantially free of R(−) fenoprofen, is combined with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citrus pulp, carboxymethylcellulose and sodium lauryl sulfate. If desired, a conventional pharmaceutically acceptable dye can be incorporated into the dosage unit form, i.e., any of the standard FD&C dyes. Sweetening and flavoring agents and preservatives can also be included, particularly when a liquid dosage form is formulated, e.g. an elixir, suspension or syrup. Also, when the dosage form is a capsule, it may contain, in addition to materials of the above type, a liquid carrier such as a fatty oil. Various other materials may be present as coatings or to otherwise modify the physical form of the dosage unit. For instance, tablets, pills or capsules may be coated with shellac and/or sugar. Such compositions should preferably contain at least 0.1% of S(+) fenoprofen; generally, S(+) fenoprofen will be from about 2% to about 60% of the weight of the unit. Typical unit dosage forms for oral administration will contain about 25 to 800 mg, preferably 50 to 300 mg, most preferably 100 to 200 mg, S(+) fenoprofen, if formulated for immediate release, as is preferred. If the composition is intended for sustained release, much larger amounts of the active ingredient would of course be incorporated into an individual unit; in such case, at least 25, and preferably up to 200 or 300 mg of the total amount of S(+) fenoprofen, should be formulated for immediate release so as to obtain the desired degree of enhanced analgesia and hastened onset.

A typical tablet or capsule for oral administration may contain, in addition to the selected amount of S(+) fenoprofen, the following combination of inactive ingredients/-carrier materials: amberlite, calcium phosphate, cellulose, D&C Yellow No. 10, FD&C Yellow No. 6, gelatin, iron oxide, magnesium stearate, silicone, starch, stearic acid, titanium dioxide, and other inactive ingredients.

Moreover, the compositions for use in obtaining enhanced analgesia and hastened onset in accord with the present invention may, in addition to the selected dose of S(+) fenoprofen, also contain other active ingredients and/or enhancing agents. Thus, for example, S(+) fenoprofen may be combined with such ingredients and agents as have been described for combination with racemic fenoprofen, e.g. caffeine or other xanthine derivative, a narcotic analgesic (with or without caffeine), a skeletal muscle relaxant, an antihistamine, decongestant, cough suppressant and/or expectorant. See, for example, Sunshine et al U.S. Pat. No. 4,464,376, issued Aug. 7, 1984; Sunshine et al U.S. Pat. No. 4,552,899, issued Nov. 12, 1985; Sunshine et al U.S. Pat. No. 4,558,051, issued Dec.10, 1985; and Sunshine et al U.S. Pat. No. 4,619,934, issued Oct. 28, 1986; and Sunshine et al pending U.S. Patent Application Ser. No. 815,502, filed Jan. 2, 1986.

The enhanced analgesic effect and hastened onset obtained by use of S(+) fenoprofen in comparison with racemic fenoprofen can be evaluated in animal and human studies such as those described below Antiphenylquinone Writhing Test This test is a standard procure for detecting and comparing analgesic activity and generally correlates well with human efficacy.

Mice are first dosed with the medications studied. The medications used are two dose levels of S(+) fenoprofen and two dose levels of racemic fenoprofen. The mice are then challenged with phenyl-p-benzoquinone given intraperitoneally and observed for the characteristic stretch-writhing syndrome. Lack of writhing constitutes a positive response. The degree of analgesic protection can be calculated on the basis of suppression of writhing relative to control animals run the same day. Time response data are also obtained. Observations are made early enough post-dosing to detect differences in onset. The test is a modification from the methods of Sigmund et al and Blumberg et al (Sigmund, E., Cadmus, R., and Lu, G., *Proc. Soc. Exp. Biol. and Med.* 95, 729–731, 1957; Blumberg, H., et al, *Proc. Soc. Exp. Biol. and Med.* 118, 763–766, 1965).

The Inflamed Rat Paw Test: Pressure Induced Stimuli

The method of Randall-Selitto, modified according to Winter et al, is used to ascertain the escape response threshold resulting from the application of increasing pressure to the yeast inflamed left hind paw. Drug treatment is given. The medications studied are two dose levels of S(+) fenoprofen and two dose levels of racemic fenoprofen. A constantly increasing force is applied to the paw and the "flight reaction" is observed and recorded at several points in time (Randall, L.Q., and Selitto, J.J.: *Arch. Int. Pharmacodyn., II,* 409–419, 1957; Winter, C.A., and Lars, F.: *J. Pharmacol. Exp. Therap.* 148, 373–379, 1965). Observations are made early enough post-dosing to detect differences in onset.

To establish the efficacy of the compositions of this invention in humans, patients with moderate to severe pain requiring an oral analgesic/anti-inflammatory agent, can be administered S(+) fenoprofen or racemic fenoprofen. Typical pain models include dysmenorrhea, post-operative pain, post-partum pain and dental extraction pain. Either a crossover design or a completely randomized design can be used. To determine analgesic efficacy, an observer interviews the patients as to their level of pain at subsequent periods of time. Patients are asked to subjectively estimate the time at which the medication begins to provide significant relief. Patients may be given a stopwatch to help estimate onset more accurately. Appropriate statistical methods, including survival analysis, can be used to show that the S(+) enantiomer has shorter onset and is more efficacious (Laska, E., Gormely, M., Sunshine, A., Belleville, J. W., Kantor, T., Forrest, W. H., Siegel, C. and Meisner, M., "A Bioassay Computer Program for Analgesic Clinical Trials," *Clin. Pharmacol. Ther.* 8:658, 1967; Cox, D.R., "Regression Models and Life Tables," *Journal Royal Statistical Society,* Series B, Volume 34:187–202, 1972).

S(+) fenoprofen for use in the method and compositions of the present invention can be prepared by a variety of methods, such as by resolution of racemic fenoprofen.

Marshall U.S. Pat. No. 3,600,437 describes the preparation of racemic fenoprofen and related compounds; see, in particular, Example 25 thereof. Resolution of racemic fenoprofen is also generally described in the Marshall patent and is exemplified in Example 38 thereof. Briefly, the racemic mixture is dissolved in hot ethyl acetate, d-(+)-α-methylbenzyl amine is added to afford crystalline dl-2-(3-phenoxyphenyl)-propionic acid, d-(+)-α-methylbenzylamine salt. Successive recrystallizations from hot ethyl acetate afford the pure salt, which is suspended between water and ethyl ether, acidified with HCl, washed, dried and evaporated in vacuo to yield d-(+)-2-(3-phenoxyphenyl)propionic acid. The l(−) isomer is similarly prepared using l-(−)-α-methylbenzylamine as the resolving agent.

Hayball et al, *J. Pharmacol. Exp. Ther.* 240(2), 631–636 (1987) have resolved racemic fenoprofen by fractional recrystallization of the (+)-1-methylbenzylamine salt of fenoprofen from ethyl acetate; after six recrystallizations, the salt contains 99.1% S(+) fenoprofen as measured by the HPLC (high-performance liquid chromatographic) enantiospecific assay of Sallustio et al, *Journal of Chromatography* 374, 329–337 (1986). HPLC methods other than Sallustio et al's for resolving enantiomers of fenoprofen are described by Doyle et al, *Pharm. Technol.* 9(2), 28–32 (1985), which utilizes conversion of fenoprofen to its amide derivatives for effective resolution; and Wainer et al, *J. Chromatogr.* 284(1), (1984), which utilizes conversion of the drug to 1-naphthalenemethylamide derivatives.

A method for derivatizing fenoprofen, ketoprofen and other nonsteroidal anti-inflammatory drugs with optically active amphetamine (α-methylbenzeneethanamide) has been described by Singh et al, *J. Chromatogr. Biomed. Appln.* 378, 125–135 (1986). Those authors also provide a summary of the usual methods for resolving enantiomers, i.e. (1) by direct separation on chiral HPLC or GC (gas chromatographic) columns, or (2) by diastereoisomer formation, by reaction with an optically pure resolving agent, followed by chromatographic separation on an optically inactive column. Singh et al's method is a new version of the second approach, using optically active amphetamine as the resolving agent, followed by separation of the diastereoisomers by capillary gas chromatography with nitrogen-phosphorus detection. (The acid, now in optically pure form, could of course then be regenerated from the salt as previously described). The usual method in the art utilizes optically active α-methylbenzylamine and involves preparation of the diastereoisomeric NSAID-α-methylbenzylamide directly by means of a coupling agent (e.g. 1,1'-carbonyldiimidazole) or via the NSAID acid chloride (prepared with thionyl chloride).

More generally speaking, the S(+) isomer can be separated from racemic fenoprofen by preparing a salt of fenoprofen with an alkaloid or similar resolving agent such as cinchonidine, then separating the products by fractional crystallization from a solvent in which the dextrorotatory isomer is least soluble. The d-salt can then be acid cleaved to yield S(+) fenoprofen. Compare, for example, Alvarez U.S. Pat. No. 3,637,767, issued Jan. 25, 1972, which relates to resolution of naproxen and related compounds; and Kaiser et al, *J. Pharm. Sci.* 65(2), 269–273 (1976), which relates to resolution of ibuprofen.

While S(+) fenoprofen may be conveniently obtained by resolution of racemic fenoprofen, it may also be possible to utilize a chemical or microbiological synthetic process which will provide the S(+) enantiomer directly. Schloemer U.S. Pat. No. 4,542,237 provides a chemical process for preparing α-arylalkanoic acids utilizing novel α-hydroxy alkyl aryl ketals as intermediates. As taught in column 9 of the Schloemer patent, the process is advantageous in that the α-hydroxy ketal can be resolved by well-known methods and the optically active α-hydroxy ketal thus obtained can then be used in the subject process to ultimately afford the desired acid in optically active form.

Alternatively, a microbiological process such as that described in SHELL INTERNATIONALE RESEARCH MAATSCHAPPIJ B.V.'S European Patent Appln. No. 86 200987.5, published under No. 0 205 215 on December 17, 1986, may be employed. According to the European application, a pharmaceutically active compound of the type

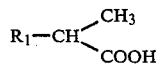

or a pharmaceutically active salt or ester thereof, which most preferably is naproxen or ibuprofen but which may be fenoprofen or various other NSAIDs, is prepared in stereospecific form by subjecting a compound of the formula

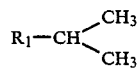

to the action of an appropriate microorganism. The desired acid is obtained having at least 70% by weight in the S-configuration. Preferably, a microorganism is selected such that the acid which is formed is at least 90% by weight in the S-configuration. Use of this method has afforded naproxen with enantiomeric distributions of 98.9% S and 1.1% R in one instance, and distributions of 99.5% S and 0.5% R in another. Processes of this type may be utilized to prepare S(+) fenoprofen for use in the present invention if the S(+) isomer can be obtained in sufficient purity.

When S(+) fenoprofen is to be employed in the form of a pharmaceutically acceptable, analgesically active salt thereof, such salt may be conveniently prepared by direct salification of S(+) fenoprofen, by well known methods. See, for example, deVincentiis U.S. Pat. No. 4,440,787, which describes salts of (2', 4'-difluoro-4-biphenyl)oxypropionic acid with metallic ions, such as sodium, potassium, magnesium and calcium, or with pharmaceutically acceptable organic bases, such as lysine, arginine and diethanolamine. Compare also Armitage et al U.S. Pat. No. 4,501,727, issued Feb. 26, 1985, which describes the N-methyl-D-glucamine salt of flurbiprofen. Such a salt may not only be used in oral or rectal compositions, but, if sufficiently soluble in water, may be useful in the preparation of aqueous solutions of S(+) fenoprofen for parenteral injection.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably and intended to be within the full range of equivalence of the following claims.

What is claimed is:

1. The method of eliciting an onset-hastened and enhanced analgesic response in a human mammal suffering from pain and in need of such treatment, comprising administering to such organism a unit dosage onset-hastening/enhancing analgesically effective amount of the S(+) fenoprofen enantiomer, and said enantiomer being substantially free of its R(−) fenoprofen antipode.

2. A method according to claim 1, wherein the weight ratio of S(+) fenoprofen to R(−) fenoprofen is greater than 9:1.

3. A method according to claim 2, wherein the weight ratio of S(+) fenoprofen to R(−) fenoprofen is greater than 20:1.

4. A method according to claim 3, wherein the weight ratio of S(+) fenoprofen to R(−) fenoprofen is greater than 97:3.

5. A method according to claim 4, wherein the weight ratio of S(+) fenoprofen to R(−) fenoprofen is approximately equal to or greater than 99:1.

6. A method according to claim 1, comprising administering to such organism from about 25 to about 800 mg S(+) fenoprofen.

7. A method according to claim 1, comprising administering to such organism from about 50 to about 300 mg S(+) fenoprofen.

8. A method according to claim 1, comprising administering to such organism from about 100 to about 200 mg S(+) fenoprofen.

9. A method according to claim 2, comprising administering to such organism from about 25 to about 800 mg S(+) fenoprofen.

10. A method according to claim 2, comprising administering to such organism from about 50 to about 300 mg S(+) fenoprofen.

11. A method according to claim 2, comprising administering to such organism from about 100 to about 200 mg S(+) fenoprofen.

12. A method according to claim 3, comprising administering to such organism from about 25 to about 800 mg S(+) fenoprofen.

13. A method according to claim 3, comprising administering to such organism from about 50 to about 300 mg S(+) fenoprofen.

14. A method according to claim 3, comprising administering to such organism from about 100 to about 200 mg S(+) fenoprofen.

15. A method according to claim 4, comprising administering to such organism from about 25 to about 800 mg S(+) fenoprofen.

16. A method according to claim 4, comprising administering to such organism from about 50 to about 300 mg S(+) fenoprofen.

17. A method according to claim 4, comprising administering to such organism from about 100 to about 200 mg S(+) fenoprofen.

18. A method according to claim 5, comprising administering to such organism from about 25 to about 800 mg S(+) fenoprofen.

19. A method according to claim 5, comprising administering to such organism from about 50 to about 300 mg S(+) fenoprofen.

20. A method according to claim 5, comprising administering to such organism from about 100 to about 200 mg S(+) fenoprofen.

21. A method according to claim 1, wherein such organism is suffering from postoperative pain.

22. A method according to claim 1, wherein such organism is suffering from postpartum pain.

23. A method according to claim 1, wherein such organism is suffering from dental pain.

24. A method according to claim 1, wherein such organism is suffering from dysmenorrhea.

25. A method according to claim 1, wherein such organism is suffering from headache pain.

26. A method according to claim 1, wherein such organism is suffering from musculoskeletal pain.

27. A method according to claim 1, wherein such organism is suffering from pain or discomfort associated with a respiratory infection.

28. A method according to claim 1, wherein such organism is suffering from pain or discomfort associated with a cold or flu.

29. A method according to claim 1, wherein such organism is suffering from pain associated with inflammatory or degenerative joint disease.

30. A method according to claim 1, wherein such organism is suffering from pain associated with rheumatoid arthritis.

31. A method according to claim 1, wherein such organism is suffering from pain associated with osteoarthritis.

32. A method according to claim 1, wherein such organism is suffering from pain associated with gout.

33. A method according to claim 1, wherein such organism is suffering from pain associated with morning stiffness.

34. A method according to claim 1, wherein the S(+) fenoprofen is orally administered to such organism.

35. A method according to claim 1, wherein the S(+) fenoprofen is rectally administered to such organism.

36. A method according to claim 1, wherein the S(+) fenoprofen is topically administered to such organism.

37. A pharmaceutical composition of matter adapted to elicit an onset-hastened and enhanced analgesic response in a mammalian organism in need of such treatment, said composition comprising a solid-state unit dosage onset-hastening/enhancing analgesically effective amount of the S(+) fenoprofen enantiomer, said enantiomer being substantially free of its R(−) antipode, and a nontoxic pharmaceutically acceptable carrier or diluent therefor.

38. The pharmaceutical composition of matter according to claim 37, adapted for oral administration.

39. The pharmaceutical composition of matter according to claim 38, formulated as a tablet, caplet, pill or capsule.

40. The pharmaceutical composition of matter according to claim 37, adapted for rectal administration.

41. The pharmaceutical composition of matter according to claim 40, formulated as a suppository.

* * * * *